(12) United States Patent
Tchakarov et al.

(10) Patent No.: US 6,627,873 B2
(45) Date of Patent: Sep. 30, 2003

(54) DOWN HOLE GAS ANALYZER METHOD AND APPARATUS

(75) Inventors: Borislav J. Tchakarov, Katy, TX (US); Rocco DiFoggio, Houston, TX (US); Stanislav W. Forgang, Houston, TX (US); Otto N. Fanini, Houston, TX (US); Marcelo F. Civarolo, The Woodlands, TX (US); James C. Hunziker, New Caney, TX (US)

(73) Assignee: Baker Hughes Incorporated, Houston, TX (US)

( * ) Notice: Subject to any disclaimer, the term of this patent is extended or adjusted under 35 U.S.C. 154(b) by 131 days.

(21) Appl. No.: 09/836,044

(22) Filed: Apr. 16, 2001

(65) Prior Publication Data

US 2002/0043620 A1 Apr. 18, 2002

Related U.S. Application Data

(63) Continuation-in-part of application No. 09/065,159, filed on Apr. 23, 1998, now Pat. No. 6,218,662.

(51) Int. Cl.[7] ................................................. G01V 8/00
(52) U.S. Cl. ..................... 250/256; 250/255; 250/269.1
(58) Field of Search ............................. 250/255, 256, 250/269.1; 73/152.28, 152.55

(56) References Cited

U.S. PATENT DOCUMENTS

| | | |
|---|---|---|
| 4,297,088 A | 10/1981 | Akkerman ................... 417/378 |
| 4,994,671 A | 2/1991 | Safinya et al. ............... 250/255 |
| 5,167,149 A | 12/1992 | Mullins et al. |
| 5,201,220 A | 4/1993 | Mullins et al. |
| 5,332,901 A | 7/1994 | Eckles et al. ................ 250/345 |
| 5,340,987 A | 8/1994 | Eckles et al. ................ 250/345 |
| 5,357,113 A | 10/1994 | Liston et al. ................ 250/344 |
| 5,457,320 A | 10/1995 | Eckles et al. ................ 250/345 |
| 5,464,982 A | 11/1995 | Drucker et al. ............. 250/343 |
| 5,559,333 A | 9/1996 | Araya et al. ................. 250/344 |
| 5,585,635 A | 12/1996 | Graham ....................... 250/343 |
| 5,635,631 A | 6/1997 | Yesudas et al. |
| 5,691,809 A * | 11/1997 | Tackett et al. ................. 356/72 |
| 6,058,773 A | 5/2000 | Zimmerman et al. ..... 73/152.24 |
| 6,437,326 B1 * | 8/2002 | Yamate et al. ........... 250/269.1 |

OTHER PUBLICATIONS

"Near–Infrared Molecular Emission from a Gas Fountain", Authors: Bonnie A. Nelson–Avery and David C. Tilotta, Publication: Applied Spectroscopy, vol. 48, No. 12, Aug. 1994, pp. 1461–1467.

"Real–Time Analysis of Light Alkenes at Elevated Temperatures and Pressures by Fiber–Optic Near–Infrared Spectroscopy", Authors: E.D. Yalvac, M.B. Seasholtz, M.A. Beach, and S.R. Crouch; Publication: Applied Spectroscopy, vol. 51, No. 10, Mar. 1997, pp.1565–1572.

"Linearity of Near–Infrared Spectra of Alkanes", Authors: Oliver C. Mullins, Nikhil B. Joshi, Henning Groenzin, Tim Daigle, Chris Crowell, M.T. Joseph, and Abul Jamaluddin; Publication: Applied Spectroscopy, vol. 54, No. 4, Jan. 2000, pp. 624–629.

* cited by examiner

*Primary Examiner*—Constantine Hannaher
(74) *Attorney, Agent, or Firm*—Madan, Mossman & Sriram, P.C.

(57) ABSTRACT

A logging while drilling and wire line system for analyzing the concentration of carbon dioxide or another substance, in a sample down hole in a bore hole. A chamber is filled with a sample that may be fluid, or condensate and gas. The interior chamber volume is selectably expandable for decompression of the sample. The sample may alternately be decompressed by allowing a sample at formation pressure to enter the chamber at a lower pressure, thereby decompressing the sample. A sensor measures the absorbance, transmittance or attenuated total reflectance of the infrared light. Mid and near infrared light is utilized to identify carbon dioxide, water and a plurality of hydrocarbons. A wiper cleans the transmitter and sensor between readings to reduce measurement error caused by fluid sample contamination.

26 Claims, 4 Drawing Sheets

DOWN HOLE GAS ANALYZER METHOD AND APPARATUS

CROSS REFERENCE TO RELATED APPLICATIONS

This patent application is a continuation in part of U.S. patent application Ser. No. 09/065,159 entitled "Downhole Carbon Dioxide Gas Analyzer," by Tchakarov et al. Filed Apr. 23, 1998 now U.S. Pat. No. 6,218,662.

BACKGROUND OF THE INVENTION

The present invention relates to the field of gas analysis downhole in a hydrocarbon producing well. More particularly, the present invention relates to a system for analyzing carbon dioxide concentration downhole in a borehole during logging while drilling or wireline operations.

Hydrocarbon producing wells contain numerous formation liquids and gases including methane, ethane, carbon dioxide, hydrogen sulfide, and other gaseous compounds. Deep wells produce fluids at extremely high temperatures. The detection and analysis of gas concentrations provides information useful in evaluating the commercial value of a hydrocarbon producing well. Numerous systems have been developed to evaluate borehole fluid composition and the relative gas concentrations in the borehole fluid.

In U.S. Pat. No. 5,167,149 to Mullins et al. (1992) and in U.S. Pat. No. 5,201,220 to Mullins et al. (1993), a borehole apparatus detected the presence of gas within a formation fluid sample. A light source transmitted light to an interface between the fluid sample and a flow line, and a detector array sensed reflected light rays having angles of incidences between the Brewster angle and the critical gas angle. A processor determined the percentage of gas by comparing the detected information to information stored in a data base. The processor also categorized the fluid sample as high gas, medium gas, and low gas.

A method for determining the quantity of dissolved gas in a sample was disclosed in U.S. Pat. No. 5,635,631 to Yesudas et al. (1997), wherein the pressure and volume of a sample were first measured. The sample pressure was changed by expanding the sample until the pressure/volume relationship was non-linear, and the sample was expanded to determine the point at which pressure was unchanged. A bubble point for the sample was determined, and the sample pressure and the bubble point volume was determined. The dissolved gas volume was then calculated by linearly scaling the bubble point volume and the extrapolated sample volume relative to the difference between the second volume and the bubble point volume.

Other systems have been disclosed to evaluate gas composition within a formation fluid. U.S. Pat. No. 4,994,671 to Safinya et al. (1991) disclosed a borehole logging tool for analyzing the composition of formation fluids. Specifically, the apparatus used near infrared spectral analysis to determine quantities of gas, water and oils in a hydrocarbon fluid. A light source emitted near infrared rays in a wavelength range between 0.3 and 2.5 microns, and a spectral detector sensed the spectrum of backscattered and transmitted rays. A data base stored the sensed data, and a processor determined the fluid composition by evaluating the near infrared absorption spectral information. The source spectrum and either the transmitted or backscattered light spectra were compared to known spectral data. After the bubble point or dew point was identified, the low line pressure was increased above such point by controlling the fluid flow rate or by moving the logging tool to an appropriate depth within the borehole.

In certain boreholes containing formation fluids combining various liquids and gases, carbon dioxide occupies substantial volumes relative to the amount of recoverable hydrocarbons. As the formation fluids are produced to the wellbore surface, hydrocarbon gases are separated from the noncommercial carbon dioxide because the economic value of carbon dioxide relative to the hydrocarbons is low. Although carbon dioxide has been historically discharged into the ambient surroundings, global warming issues may discourage this form of gas separation and disposal. Carbon dioxide is also reinjected into subsurface geologic formations, however re-injection wells are expensive and may be impractical in certain geographic regions.

Accordingly, a need exists for a system capable of accurately evaluating the presence and quantity of carbon dioxide downhole in a borehole so that zones containing high levels of carbon dioxide can be avoided. The system should accurately identify the carbon dioxide concentration under different pressures, temperatures and wellbore conditions, and should provide real-time logging capabilities before borehole completions operations are performed. There is also a need to provide carbon dioxide measurements can be provided to an operator at the surface, or a processor or intelligent completion system. There is also a need for a carbon dioxide measurement device for logging while drilling and wire line operations for steep incline and horizontal drilling well bores. The is also a need for a reliable carbon dioxide measurement device for two-phase, condensate and gas samples for logging while drilling and wire line operations for steep incline and horizontal drilling well bores.

SUMMARY OF THE INVENTION

The present invention provides an apparatus and method for analyzing the carbon dioxide concentration in a fluid sample downhole in a borehole. The carbon dioxide measurement is utilized as an input to an intelligent completion system. The apparatus comprises a chamber defining an initial volume for containing the fluid sample, optionally expanding the chamber initial volume to decompress the fluid sample, and a transmitter for discharging mid-infrared light. The initial sample volume is selectable and when desired, the initial unexpanded volume is selected to substantially fill the sample tank. The sample volume is adjustable precisely between a minute sample volume to a tank full. All sample volumes selected are selectably decompressed by expanding the initial sample chamber volume, however, the initial sample volume is not expanded when decompression is not selected. A sensor measures the absorption or attenuated total reflectance of near and mid-infrared light of the decompressed or not decompressed fluid sample and generates a signal representing the carbon dioxide concentration in the fluid sample. A processor receives the signal and determines the fluid sample carbon dioxide concentration.

In different embodiments of the apparatus, the sensor can measure infrared absorbance in ranges between 4.1 and 4.4 microns or measure attenuated total reflectance to identify carbon dioxide concentration, and between 3.2 and 3.6 microns to provide data representing methyl and methylene concentrations. Other selectable wave numbers for methane comprise 1667, 2200, 2318, and 2372. The chamber expanding means optionally expands the chamber initial volume until the fluid sample is substantially one hundred percent gas phase, and a wiper for cleaning the transmitter and the sensor between successive measurements can reduce measurement errors.

Accordingly, a need exists for a system capable of accurately evaluating the presence and quantity of carbon dioxide downhole in a borehole so that zones containing high levels of carbon dioxide can be avoided. The system should accurately identify the carbon dioxide concentration under different pressures, temperatures and wellbore conditions, and should provide real-time logging capabilities before borehole completions operations are performed. There is also a need to provide carbon dioxide measurements can be provided to an operator at the surface, or a processor or intelligent completion system. There is also a need for a carbon dioxide measurement device for logging while drilling and wire line operations for steep incline and horizontal drilling well bores. The is also a need for a reliable carbon dioxide measurement device for two-phase, condensate and gas samples for logging while drilling and wire line operations for steep incline and horizontal drilling well bores. The method of the invention comprising the steps of deploying a chamber into the borehole to define an initial chamber volume, of moving the fluid sample into the chamber volume, of closing said chamber to isolate the fluid sample from the borehole, and of optionally expanding said initial chamber volume to decompress the fluid sample. A transmitter is operated to discharge near or mid-infrared light, and an absorbance sensor or an attenuated total reflectance probe is operationally positioned and operated to measure the fluid sample near or mid-infrared light absorbance or attenuated total reflectance. The present invention generates a signal representing the carbon dioxide concentration, or other material or gas detected. The measurement signal is provided as an input signal to an intelligent completion system (ICE). The ICE or a dedicated processor receive and store the signal from the sensor. The ICE or processor are selectably operated to determine the carbon dioxide concentration.

In horizontal drilling operations when measuring carbon dioxide for a condensate/gas sample an orientation sensor is provided to ensure that the tool is oriented so that the infrared transmitter/sensor is positioned in the top portion of the sample where the gas is gathered above the condensate.

DETAILED DESCRIPTION OF A PREFERRED EMBODIMENT

The present invention provides an apparatus and method for analyzing the carbon dioxide concentration of a fluid sample downhole in a borehole. The invention permits the carbon dioxide concentration to be surveyed downhole so that perforating and well production operations can avoid high carbon dioxide zones, thereby reducing expenses for gas separation, re-injection wells and other production operations.

Figures 1, 4, 5, 6, 7, 8:
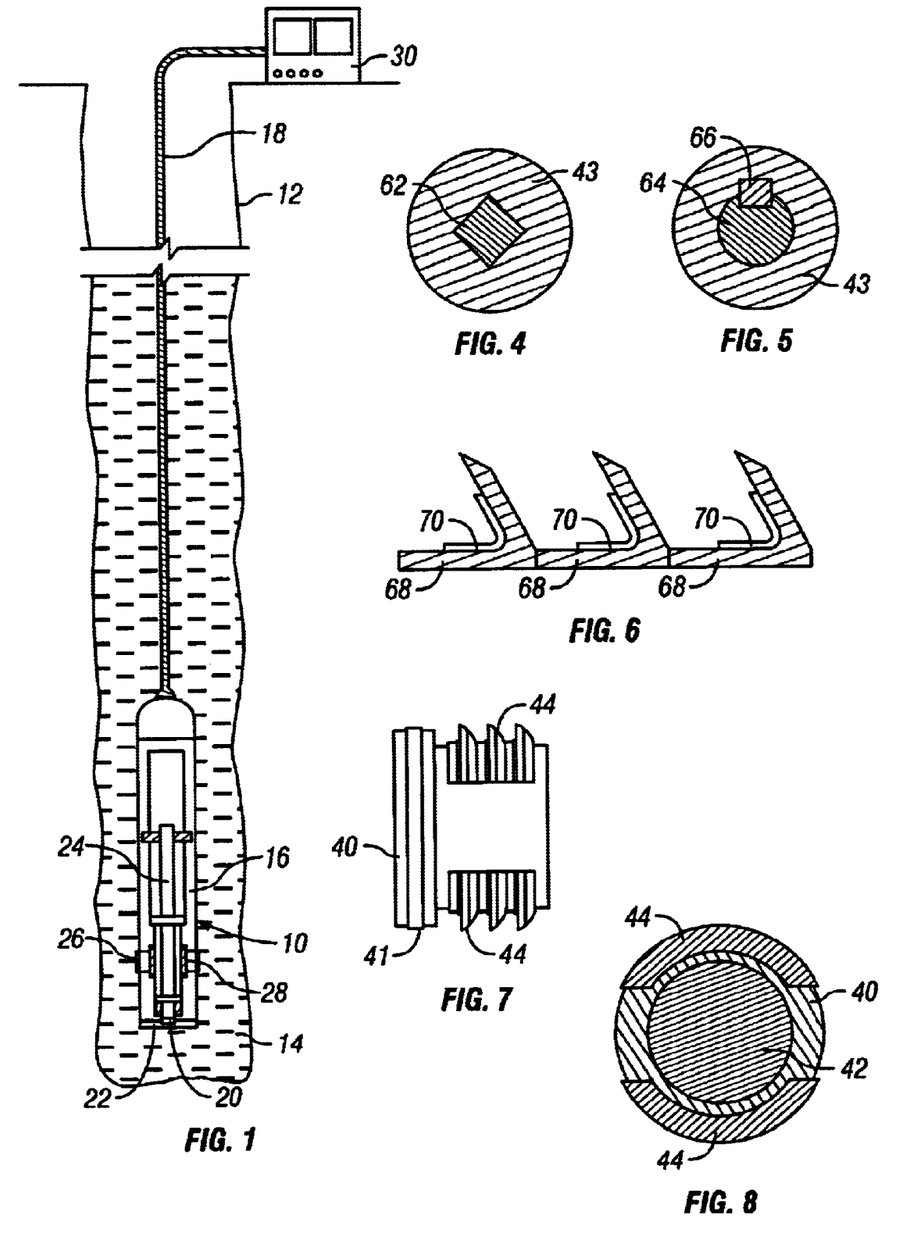
FIG. 1 illustrates a carbon dioxide logging tool downhole in a wellbore.
FIGS. 4 and 5 illustrate different profiles for the piston shaft.
FIG. 6 illustrates one profile for a wiper seal combination.
FIGS. 7 and 8 illustrate one configuration of a wiper element.

FIG. 1 illustrates logging tool 10 located downhole in borehole 12. Fluid 14 from subterranean formations flows into borehole 12 and can be selectively produced to the wellbore surface. As used herein, the term "fluid" refers to liquids and gases typically under compression within the subterranean geologic formations. The fluid pressures in deep boreholes can be 20,000 psi or greater, thereby reducing carbon dioxide and other gases to a liquid phase.

Tool 10 comprises housing 16 attached to wireline 18. Housing 16 includes chamber 20 defining an interior space or initial volume 22 having known dimensions. Decompression cylinder shown as hydraulic cylinder 24 defines the size of chamber 20 within housing 16 and is moveable to selectively increase the size of initial volume 22, thereby decompressing any fluid sample initially positioned within initial volume 22 as described below. Transmitter 26 discharges mid-infrared light, and sensor 28 detects mid-infrared light that is not backscattered or absorbed by fluid 14. Sensor 28 generates signal as described below and transmits such signal to processor or intelligent completion system (ICE) 30 for receiving, storing and processing the signal or combination of signals.

Figure 2:
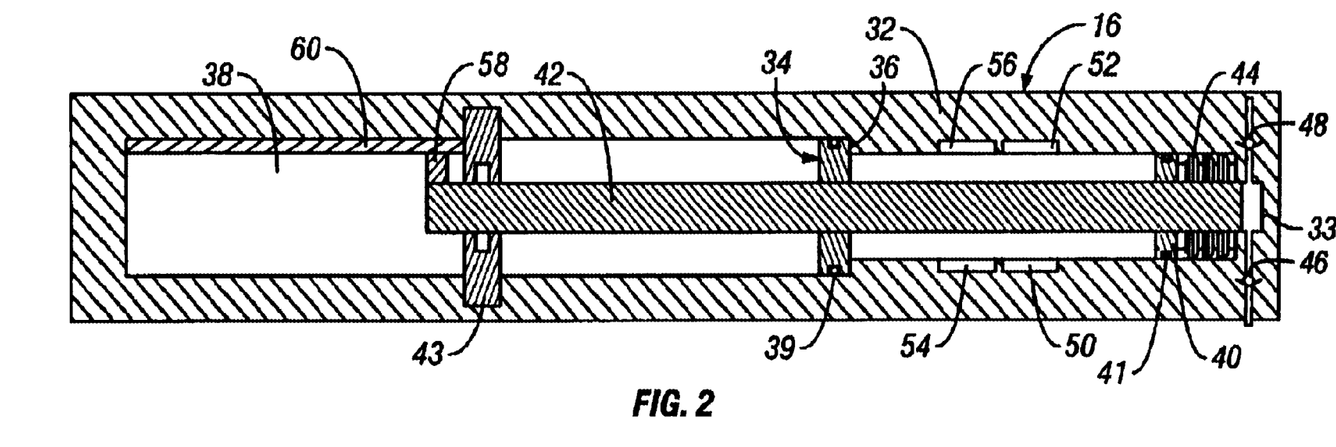
FIG. 2 illustrates a logging tool after a fluid sample is introduced into the interior chamber of the tool.

Referring to FIG. 2, one embodiment of logging tool 10 is shown. Housing 16 is shown as cylindrical tube 32. Initial volume 33 comprises a relatively small space located at one end of tube 32. Moveable cylinder 34 has piston head 36 movable by a suitable means such as moveable device 38. Piston head 34 includes seal 39 for preventing leakage of hydraulic or another fluid. Device 38 can comprise any hydraulic, mechanical, electrical or similarly powered means for moving piston head 34. Seal 39 attached to piston head 34 and prevents leakage of hydraulic fluid or another fluid through the clearance between piston head 34 and cylindrical tube 32, stop 39 is positioned within cylindrical tube 32, and decompression piston 40 having dynamic seal 41 is attached to one end of piston shaft 42. Piston shaft 42 is reciprocal within cylinder tube 32 and is guided by an aperture through stop 37 and by the outer radius of piston head 36. Piston shaft 42 can extend through piston head 36 and is attached to piston head 36 and to wiper 44 so that movement of piston shaft 42 also moves piston head 36 and wiper 44. In one embodiment of the invention as illustrated, wiper 44 is attached to decompression piston 40 or can be integrated into decompression piston 40 in other configurations.

Figure 3:
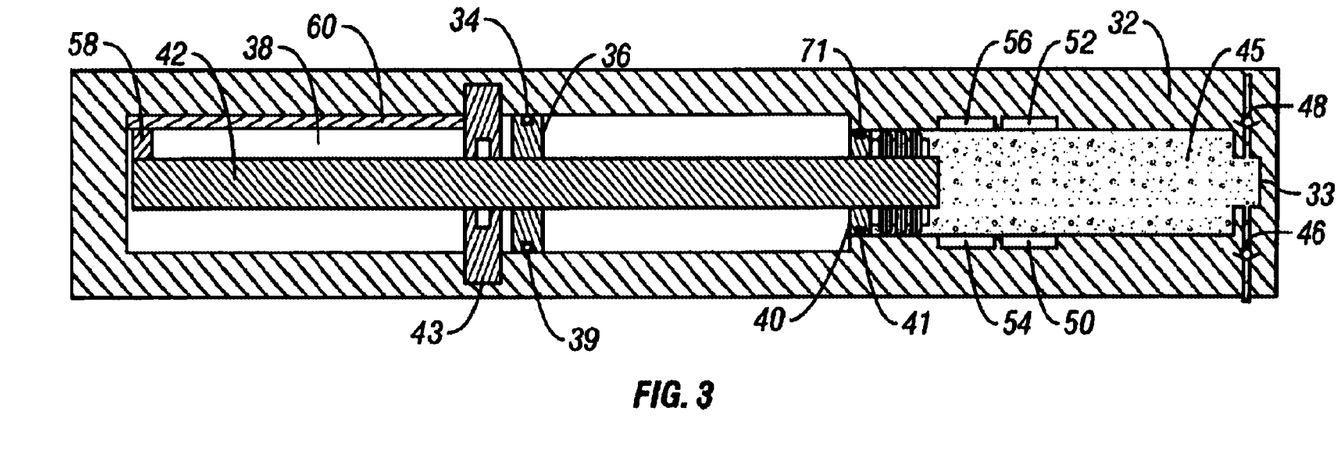
FIG. 3 illustrates the fluid sample within the measurement chamber after the fluid has been decompressed.

Wiper 44 scrubs the interior wall of cylindrical tube 32 and can cooperate with decompression piston 40 to define the space identified as measurement volume 45. Measurement volume 45 is illustrated in FIG. 3 as the space opened by movement of wiper 44 within cylindrical tube 32, combined with the space defined by initial volume 33. As defined herein, measurement volume 45 provides the final volume for the fluid sample after decompression of the fluid sample is performed.

Inlet valve 46 selectively permits the entry of borehole fluid 14 into initial volume 33, and discharge valve 48 selectively permits the discharge of borehole fluid 14 out of initial volume 33. Although inlet valve 46 and discharge valve 48 could comprise the same valve or valve combination, using two valves permits a flowthrough passage of the fluid sample through initial volume 33 to reduce potential contamination of each fluid sample as successive samples are tested and to avoid commingling of successive samples.

After a fluid sample has been introduced into measurement volume 45 and the sample has been decompressed so that the target gas comprises one hundred percent gaseous phase, the composition of the gas can be assessed. Decompression may be accomplished by expanding the chamber volume after an initial sample is sealed in the sample chamber or by allowing a sample to invade an evaluated or decompressed sample chamber. Decompression is selectable and is not always used on a sample.

Transmitter 50 is engaged with tube 32 and corresponding sensor 52 is positioned opposite of tube 32. Other combinations of instruments such as transmitter 54 and corresponding sensor 56 can be similarly engaged with tube 32 as described below. Position sensor 58 is attached to piston shaft 42, and reading sensor 60 identifies the relative location of position sensor 58. Different mechanisms for measuring the relative position of shaft 42 can be created to monitor and verify the orientation and operation of logging tool 10.

The near-infrared (NIR) region of the electromagnetic spectru offers advantages over the infrared region for the acquisition of spectral information. The advantages include the elimination of special optical components, the convenience of atmospheric transparency and the extension of the linear dynamic range to fairly large concentrations of the analyte.

In operation, inlet valve 46 and discharge valve 48 are opened to draw a fluid sample of borehole fluid 14 through interior volume 33. Discharge valve 48 is closed, and inlet valve 46 is then closed to isolate the known fluid sample quantity of fluid 14 at an initial volume correlating to initial volume 33 and to contain the fluid 14 sample. When decompression has been selected, piston shaft 42 and decompression piston 40 are moved to the position shown in FIG. 3. This movement enlarges the space of initial volume 33 into measurement volume 45. This piston shaft 42 movement decompresses the fluid sample by increasing the volume occupied by such fluid sample. The extent of such movement is volume 33 could comprise a minutely small clearance between the end of cylinder 24 and the intake portion of chamber 20, together with the inlet lines between the valves 46 and 48 and cylinder 24. The accuracy of subsequent measurements will depend on the initial fluid sample size, the amount of decompression obtained, the nature of contaminants in the fluid sample, the temperature of the fluid sample, and other variable factors.

After the fluid sample is captured and if decompression is desired, after the sample is decompressed to a selected level, transmitters 50 and 54 discharge light rays in selected wavelength ranges, and sensors 52 and 56 can detect transmitted light rays corresponding to the respective transmitters. The transmission frequency can be varied to help distinguish and analyze peaks that are, close together or peaks that appear on the slope of another peak. The frequency variations enable detection of a first peak in the presence of a second peak that may be larger and/or close in frequency to the first peak. In a preferred embodiment of the invention, transmitter 50 discharges mid-infrared light in a range between 4.1 to 4.4 microns. This range comprises a preferred range for carbon dioxide absorbance. Using Beer's Law and assuming a fixed pathlength, the amount of carbon dioxide in the fluid sample is proportional to the absorption of light in this preferred range. In another embodiment of the invention, transmitter 54 discharges mid-infrared light in a range between 3.2 to 3.6 microns, which comprises a preferred range for absorbance of methyl and methylene functional groups. Data collected from these two frequency ranges provides information for precisely determining the ratio of carbon dioxide to hydrocarbon gases predominately comprising methyl and methylene.

The absorbance of mid-infrared emitted light within these ranges is influenced by fluid 14 composition and by environmental factors. At high temperatures, mid-infrared light sensors become noisy. Interference from absorbance by other molecules in the range between 4.1 and 4.4 microns should not interfere with the carbon dioxide measurements because other molecules absorbing light in such range, such as alkynes and nitriles, typically comprise unstable triple-bonded compounds not typically found in natural gas and other downhole formation fluids. If an interfering molecule is resident within the fluid sample, additional wavelengths can be measured with other transmitters or a multiple frequency transmitter and sensors to compensate for and to distinguish the interfering molecule.

A transmitter and sensor are also be provided to respectively emit and detect near-infrared light. Additional gases and hydrocarbon condensate/gases can be detected using a plurality of wave lengths indicative of the presence of a detectable gas or condensate. Near infrared light is transmitted by transmitters 50 and/or 54 through the sample and detected by sensors 52 and 56 for absorbance. Attenuated total reflectance probes are provided for measurement of attenuated total reflectance to detect and distinguish gas and condensate molecules present in the sample chamber. Additional carbon dioxide wavelengths, for example, 1430 nm, 1957 nm, 2007 nm or 2057 nm are utilized to sense carbon dioxide. In addition methane and other hydrocarbon wavelengths in general can be sensed and detected.

By measuring the amount of light detected by sensor 52, the amount of carbon dioxide absorbance within fluid 14 can be determined, and a signal representing this information can be transmitted to processor or intelligent completion system (ICE) 30 for storage or for smart well ICE or data processing operations. Processor/ICE 30 can be operated to determine the carbon dioxide concentration with fluid 14 through the application of processing techniques known in the art. Similarly, a signal representing aborbance or attenuated total reflectance is generated by sensor 56 and transmitted to processor 30 for storage and data processing. After the selected measurements are taken, inlet valve 46 and discharge valve 48 are opened, shaft 42 is reciprocated toward the initial position, and the fluid sample is discharged from the interior of logging tool 10. The orientation and operation of discharge valve 48 or a discharge port (not shown) can be positioned to permit through flow of the fluid sample through logging tool 10 to prevent contamination of fluid 14 measurements.

The ICE is a system for the remote, interventionless actuation of downhole completion equipment developed to support the ongoing need for operators to lower costs and increase or preserve the value of the reservoir. Such a system is described in The Oil and Gas Journal, Oct. 14, 1996. These needs are particularly important in offshore environments where well intervention costs are significantly higher than those performed onshore. For example, traditional methods for setting a production packer employ coiled tubing or slickline to run a tubing plug. The new system provides a safe, reliable and more cost efficient alternative to this method because it simply transmits acoustic pulses through the contents of tubulars to actuate one or more completion or service tools remotely in any desired sequence. The system not only decreases the time to set the packer but also extends the envelope for application to deep, extended-reach offshore environments. Since the system eliminates the need to circulate a ball downhole to set service tools during sand control operations, the operator can maintain constant hydrostatic pressure on the formation. This capability decreases completion time, intervention risk, the possibility of formation collapse against the completion string, the possibility of losing the filter cake placed against the formation, and fluid loss to the formation. To achieve the goals required for this system, three project targets were addressed: a reliable means of wireless communication, a surface control system, and a downhole power unit for completion device actuation. The design and capabilities of the new surface-operated, non-intervention completion system will facilitate economic completions in situations where more complex systems could not be justified, thus increasing the scope of application for 'intelligent well' technology.

At times called "SmartWells," these completion systems will allow oil and gas companies to study and control individual zones without well intervention. This can dramatically lower operating expenditures by reducing downtime. Also, it can allow enhanced hydrocarbon recovery via improved reservoir management. ICEs enable the operator to produce, monitor and control the production of hydrocarbons through remotely operated completion systems. These systems are developed with techniques that allow the well architecture to be reconfigured at will and real-time data to be acquired without any well intervention.

The operator, located at the surface and having access to over ride the processor/ICE 30 may make his own decisions and issue his own commands or let the processor/ICE make decisions and issue commands concerning well completion, adjustment of production flow, reinjection or other well modifications, based on the measurements provided by the present invention. Referring to FIGS. 4 and 5, various techniques are illustrated for maintaining a constant orientation of shaft 42 relative to the other components, and for maintaining the orientation of wiper 44 relative to transmitters 50 and 54 and sensors 52 and 56. FIG. 4 illustrates a rectangular shaft 62 to accomplish this function, and FIG. 5 illustrates cylindrical shaft 64 linearly guided with key 66 operating within a corresponding slot or keyway (not shown) within stop 43. Other mechanical devices and orientations can be utilized to constrain the movement of shaft 42, or to avoid restraints on the rotational movement of shaft 42.

In various embodiments of the invention, transmitters 50 and 54, and sensors 52 and 56, can be in optical contact with the interior space of cylindrical tube 32 through glass windows or other transparent or translucent materials. When fluid 14 is run into and out of such interior space, contaminants within fluid 14 can be deposited on such materials and can interfere with accurate readings of light transmission and detection. To reduce errors caused by such contaminants, wiper 44 removes fluid 14 contaminants from the surfaces of transmitters 50 and 54 or from the surfaces of sensors 52 and 56. Wiper 44 accomplishes this cleaning means function as shaft 42 is reciprocated in both directions to move wiper 44 within cylindrical tube 32, and can clean the internal components immediately before absorption measurements are performed.

FIG. 6 illustrates detail for one form of wiper 44 wherein seals 68 are attached to shaft 42 and are stacked to provide redundant cleaning capabilities. Seals 68 can be formed with different materials including Peek material and Viton material, and can comprise different structural shapes and configurations. As shown in FIG. 6, springs 70 can provide structural support for the wiping elements of seals 68. Although seals 68 are oriented in one direction, other seal designs can provide for similar cleaning action regardless of the movement direction of seals 68. Although linear movement of seals 68 is illustrated, rotation of shaft 42 could be performed to accomplish different cleaning movements.

FIG. 7 illustrates one embodiment of decompression piston 40 wherein wiper 44 is attached to decompression piston 40. Although seal 41 can prevent fluid migration past piston 40, seal 41 does not adequately clean transmitters 50 and 54 or sensors 52 and 56.

FIG. 8 further illustrates another view of wiper 44 taken in section through wiper 44, and showing one potential orientation relative to shaft 42.

Figure 9:
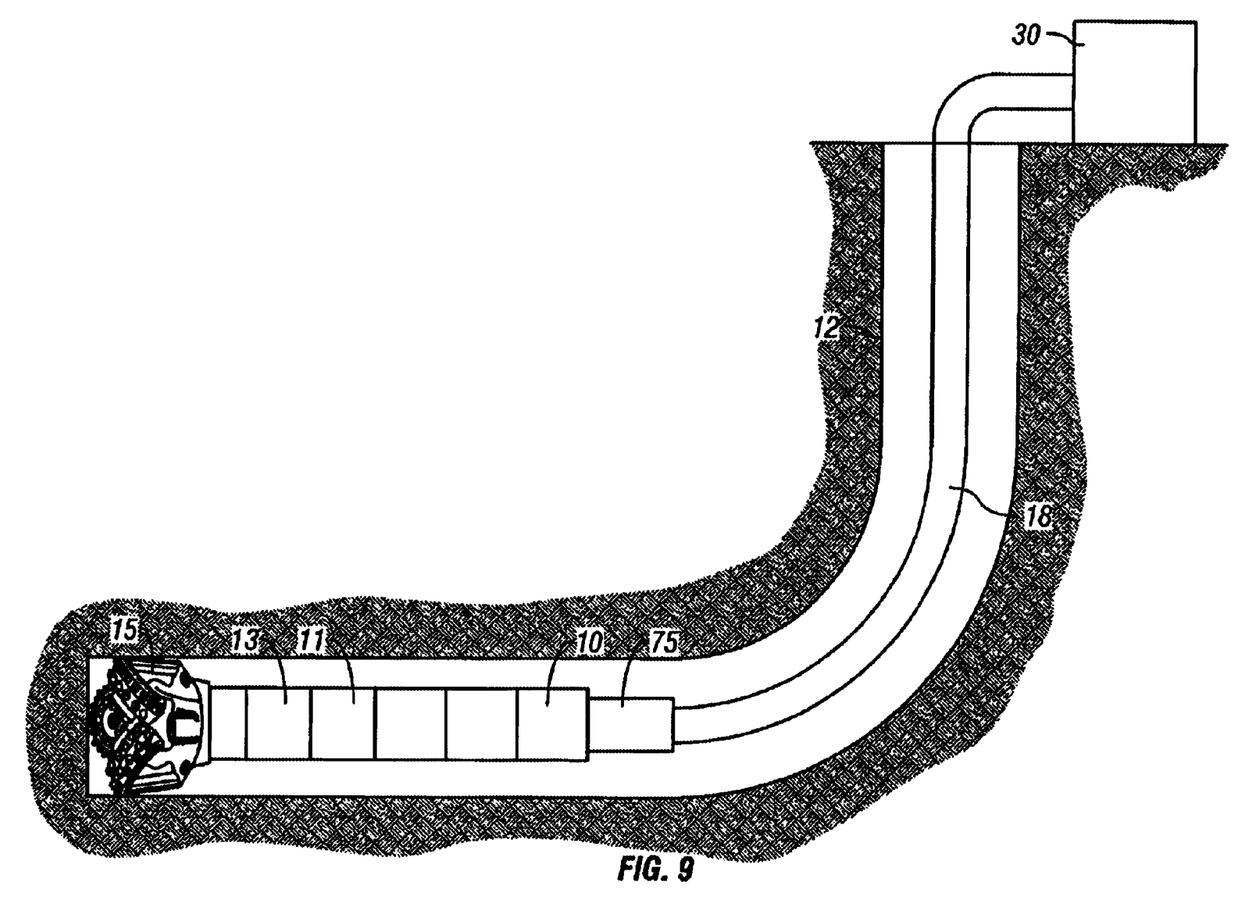
FIG. 9 illustrates a logging while drilling application of the present invention.

FIG. 9 illustrates the use of the present invention in a horizontal or steep incline logging while drilling application. As shown in FIG. 9, a drill string, which can optionally comprise production drill pipe 18 or coiled tubing, drill bit 15 and heavy wall drill pipe 75 is drilling a horizontal or steeply inclined well bore 12. The bottom hole tool assembly 13 and drill bit 15 are drilling the horizontal borehole. A preferred embodiment of the present invention, an infrared detection module 10 is shown as part of the logging while drilling system. In wire line operations or logging while drilling operations, well known orientation sensing devices are provided to sense the rotational orientation of the tool and attached measuring device of the present invention. The well-known orientation devices sense the vertical orientation or high side of the tool. The signal generated by the detector is provided as an input to the ICE or processor 30 at the surface. For example, in a logging while drilling scenario utilizing the present invention, a power swivel is utilized to rotate the measuring device in accordance with the position determined by accelerometers and magnetometers, to determine where the high side of the tool is (that is, looking straight up), thus the power swivel rotates the measurement module so that it will be oriented up, toward the high side. A second option is to rotate the drill string from the surface until proper orientation is achieved. In a wire line scenario, utilizing the present invention, passive orientation devices are attached, for example, decentralizing arms, eccentric weights, cork screw type orientation device or power swivels which are utilized to rotate the tool string or the measurement module. Thus, the measuring device is oriented in high inclination wells and horizontal wells toward for the high side. In both cases the orientation devices provide the orientation of the high side of the tool.

Figure 10:
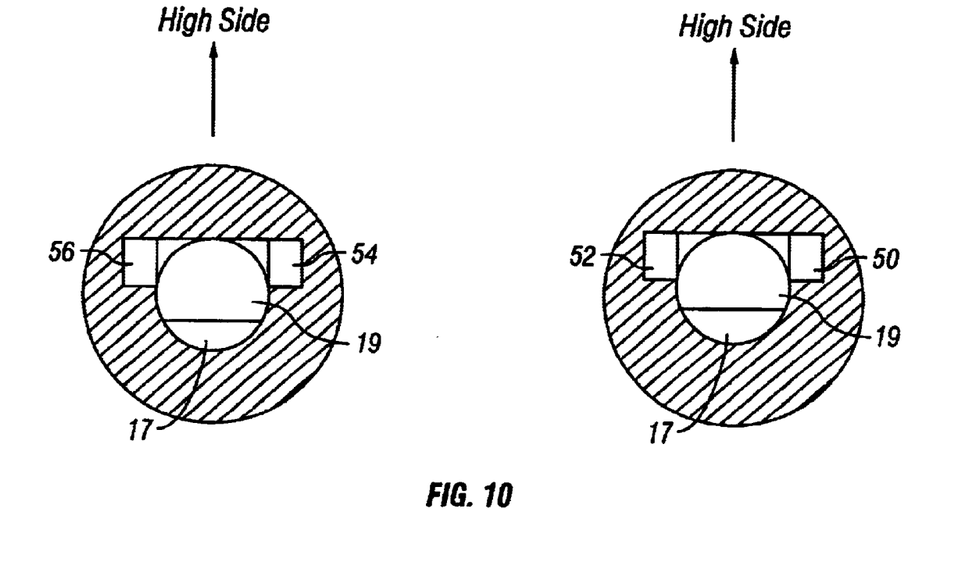
FIGS. 10A and 10B illustrates a cross section of the sample chamber of the present invention showing the infrared emitter and sensor positioned above condensate in the gaseous area of the sample chamber.

Turning now to FIG. 10, the present invention is in a known orientation relative to the drill pipe orientation. When sampling condensate and condensate/gaseous samples, the present invention enables the operator or some other automatic sensing and positioning system located down hole or on the surface in the ICE/processor 30, to orient the vertical position the drill pipe and attached analyzer module 10 so that the tunable transmitters 50 and 54 and sensors 56 and 52 are at the top of the sample chamber so that they are above the condensate and in the gaseous portion of the sample within the sample chamber. Attenuated total reflectance probes can also be operationally oriented so that they are positioned above the condensate and in the gaseous portion of the sample within the sample chamber. In cases where decompression is not selected, by the operator or ICE/processor, the sample chamber is analyzed without decompression. The sample chamber is selectably filled to a precise known volume and can be substantially a full volume or reduced. The present invention analyzes the sample with or without decompression.

Figure 11:
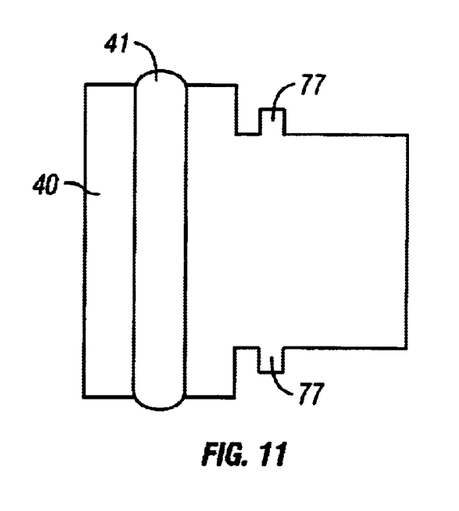
FIG. 11 illustrates an alternative embodiment of the present invention providing a sprayer for cleaning the infrared transmitter and sensor windows.

FIG. 11 illustrates an alternative embodiment of the present invention providing a sprayer for cleaning the infrared transmitter and sensor windows. The sprayers 77 spray pressurized gas, air, or fluid toward the infrared transmitter and sensor windows, gaps or apertures to clean the windows and any lens which may be placed in the window. A focusing lens is provided for placement in the window for the transmitter or sensor thereby focusing or converging the transmitted or received infrared energy to obtain a higher intensity response or defocusing or diverging the transmitted or received energy to hit additional molecules with the infrared emission and receive from a broader area.

Figure 12:
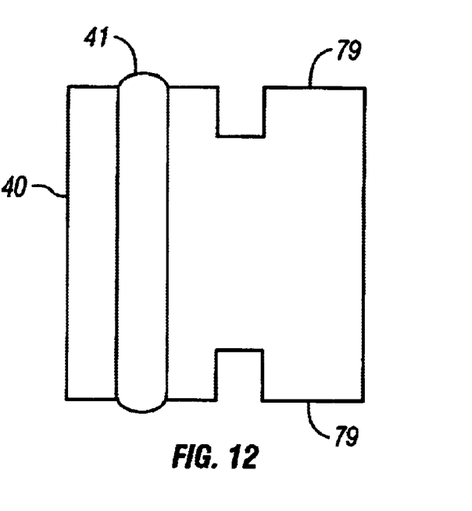
FIG. 12 illustrates an alternative embodiment of the present invention providing a cleaning surface for rotational cleaning of the transmitter and sensor window.

FIG. 12 illustrates an alternative embodiment of the present invention providing a cleaning surface for rotational cleaning of the transmitter and sensor window by rotating cleaning surface 79 inside of the chamber and against window or gap or aperture to clean the window gap or aperture and any focusing or defocusing lens inserted therein.

While a preferred embodiment of the present invention has been illustrated, the example presented is not intended to limit the scope of the present invention which is defined by the following claims.

What is claimed is:

1. A bore hole apparatus for analyzing the carbon dioxide concentration in a sample down hole in a bore hole, comprising:

a chamber having a piston for defining an initial sample volume in the chamber for containing an initial fluid sample wherein the piston is slidably disposed within the chamber for selectively expanding the chamber initial volume of the chamber and decreasing the pressure within the chamber to decompress the fluid sample;

a transmitter for discharging infrared light a first sensor for measuring at least one of absorption, transmittance or attenuated total reflectance of infrared light for the fluid sample and for generating a signal representing the carbon dioxide concentration in the fluid sample; and a processor for receiving said signal and for determining the fluid sample carbon dioxide concentration.

2. An apparatus as recited in claim 1, wherein the signal is transmitted to the surface for an operator or an intelligent completion system to adjust completion.

3. An apparatus as recited in claim 2 further comprising a second sensor for measuring at least one of infrared absorbance or attenuated total reflectance in a range suitable for detection of selected hydrocarbon gases.

4. An apparatus as recited in claim 3, further comprising a third sensor suitable for detection of an interfering molecule resident within the fluid sample.

5. An apparatus as recited in claim 1, wherein the piston is capable of precisely expanding the expansion chamber initial volume of the fluid sample, and precisely controlling the initial volume of the initial fluid sample until the fluid expands to transform to its substantially one hundred percent gas phase.

6. An apparatus as recited in claim 1, further comprising a wiper disposed inside of the chamber for cleaning the inside of the chamber.

7. An apparatus as recited in claim 6, wherein the wiper is attached to the piston so that the wiper cleans the inside of the chamber during at least one of: compression or decompression of the chamber so that at least one of a sensor window or a transmitter window is cleaned.

8. An apparatus as recited in claim 1, further comprising a wiper disposed in the chamber, wherein the transmitter and sensor are adjacent the chamber so that the wiper cleans at least one of a transmitter window and a sensor window during at least one of: compression and decompression of the chamber.

9. An apparatus as recited in claim 1, wherein the piston and an integrated wiper are integrated in the chamber for selectively expanding the initial chamber volume and for returning the apparatus to the initial chamber volume.

10. The apparatus of claim 1 wherein the signal is received by a operator or a processor at an intelligent completion station for determining the completion state of a well.

11. A bore hole apparatus for analyzing the carbon dioxide concentration in a sample down hole in a bore hole, comprising:

a chamber having a piston wherein the piston is slidably disposed within the chamber for defining an initial sample volume in the chamber for receiving an initial fluid sample, wherein the initial sample volume of the chamber is selectively expanded, to reduce the the pressure in the sample chamber to a pressure lower than the pressure of the sample prior to the sample entering the chamber, thereby selectively decompressing the sample as it enters the initial sample volume;

a transmitter for discharging infrared light;

a first sensor for measuring at least one of absorption, transmittance or attenuated total reflectance of infrared light for the fluid sample, the first sensor generating a signal representing the carbon dioxide concentration in the fluid sample; and a device for receiving said signal and for determining the sample carbon dioxide concentration.

12. The apparatus of claim 11 wherein the signal is received by a operator or a processor at an intelligent completion station for determining the completion state of a well.

13. The apparatus of claim 11 wherein the sample contains condensate and gas, further comprising an orientation device so that the infrared transmitter and sensor are positioned on the high side of the chamber so that the infrared transmitter and sensor are positioned adjacent the gaseous portion of the sample.

14. An apparatus as recited in claim 13, further comprising a wiper disposed in the chamber, wherein the transmitter and sensor are adjacent the chamber so that the wiper cleans at least one of a transmitter window and a sensor window during at least one of: compression and decompression of the chamber.

15. A method for analyzing the carbon dioxide concentration in a sample down hole in a bore hole, comprising:

providing a chamber having a piston for defining an initial sample volume in the chamber for containing an initial fluid sample wherein the piston is slidably disposed within the chamber for selectively expanding the chamber initial volume of the chamber and decreasing the pressure within the chamber to decompress the fluid sample;

providing a transmitter for discharging infrared light;

providing a first sensor for measuring at least one of absorption, transmittance or attenuated total reflectance of infrared light for the fluid sample and for generating a signal representing the carbon dioxide concentration in the fluid sample; and providing a processor for receiving said signal and for determining the fluid sample carbon dioxide concentration.

16. The method as recited in claim 15, further comprising:

transmitting the signal to the surface; and receiving the signal at the surface by an operator or an intelligent completion system to adjust at least one of: completion, production flow or reinjection.

17. The method as recited in claim 16 further comprising:

providing a second sensor for measuring at least one of infrared absorbance or attenuated total reflectance in a range suitable for detection of selected hydrocarbon gases.

18. The method as recited in claim 16, further comprising:

providing a third sensor suitable for detection of an interfering molecule resident within the fluid sample.

19. The method as recited in claim 15, further comprising:

precisely moving the piston and expanding the expansion chamber initial volume of the fluid sample, and precisely controlling the initial volume of the initial fluid sample until the fluid expands to transform to its substantially one hundred percent gas phase.

20. The method as recited in claim 15, further comprising a wiper disposed inside of the chamber for cleaning the inside of the chamber.

21. The method as recited in claim 20, wherein the wiper is attached to the piston so that the wiper cleans the inside of the chamber during at least one of: compression or decompression of the chamber so that at least one of a sensor window or a transmitter window is cleaned.

22. An apparatus as recited in claim 15, wherein a piston and an integrated wiper are integrated in the chamber for selectively expanding the initial chamber volume and for returning the apparatus to the initial chamber volume.

23. The method of claim 15 wherein the signal is received by a operator or a processor at an intelligent completion station for determining the completion state of a well.

24. A method for for analyzing the carbon dioxide concentration in a sample down hole in a bore hole, comprising:

providing a chamber having a piston wherein the piston is slidably disposed within the chamber for defining an initial sample volume in the chamber for receiving an initial fluid sample, wherein the initial sample volume of the chamber is selectively expanded, to reduce the the pressure in the sample chamber to a pressure lower than the pressure of the sample prior to the sample entering the chamber, thereby selectively decompressing the sample as it enters the initial sample volume;

providing a transmitter for discharging infrared light;

providing a first sensor for measuring at least one of absorption, transmittance or attenuated total reflectance of infrared light for the fluid sample, the first sensor generating a signal representing the carbon dioxide concentration in the fluid sample; and providing a device for receiving said signal and for determining the sample carbon dioxide concentration.

25. The method of claim 24 further comprising:

receiving the signal at the surface for determining the completion state of a well by at least one of an operator or a processor at an intelligent completion station.

26. The method of claim 24 wherein the sample contains condensate and gas, further comprising:

receiving a signal from an orientation device to determine the orientation of the sample chamber in order to find the high side of the sample chamber; and positioning the infrared transmitter and sensor on the high side of the chamber so that the infrared transmitter and sensor are positioned adjacent the gaseous portion of the sample.

* * * * *